United States Patent [19]

Alpern

[11] Patent Number: 4,572,363
[45] Date of Patent: Feb. 25, 1986

[54] SUTURE RETAINER FOR MULTISTRAND SUTURES WITH SINGLE STRAND SUTURE DISPENSING

[75] Inventor: Marvin Alpern, Glen Ridge, N.J.

[73] Assignee: Ethicon, Inc., Somerville, N.J.

[21] Appl. No.: 753,731

[22] Filed: Jul. 10, 1985

[51] Int. Cl.⁴ .............................................. A61L 15/00
[52] U.S. Cl. .................................... 206/63.3; 206/476
[58] Field of Search ...................... 206/63.3, 227, 363, 206/380, 381, 382, 388, 438, 476, 488, 489, 291, 492

[56] References Cited

U.S. PATENT DOCUMENTS

| | | | |
|---|---|---|---|
| 4,063,638 | 12/1977 | Marwood | 206/63.3 |
| 4,182,448 | 1/1980 | Huck et al. | 206/63.3 |
| 4,253,563 | 3/1981 | Komsanycky | 206/63.3 |
| 4,391,365 | 7/1983 | Batchelor | 206/63.3 |
| 4,427,109 | 1/1984 | Roshdy | 206/63.3 |
| 4,483,437 | 11/1984 | Cerwin et al. | 206/63.3 |

Primary Examiner—Joseph Man-Fu Moy
Attorney, Agent, or Firm—Robert L. Minier

[57] ABSTRACT

A folded suture retainer for multistrand sutures providing for single strand delivery of sutures from the retainers. The retainer comprises a jacket member and an insert member disposed within the jacket member. The retainer provide separate spaces for containing individual sutures in a manner to prevent kinking of the suture and entanglement with adjacent sutures.

12 Claims, 12 Drawing Figures

SUTURE RETAINER FOR MULTISTRAND SUTURES WITH SINGLE STRAND SUTURE DISPENSING

BACKGROUND OF THE INVENTION

The present invention relates to packages for surgical sutures and more particularly to a multiple panel folded retainer for a plurality of sutures which retainer allows for single strand dispensing of the sutures.

Packages for surgical sutures are constructed according to the nature of the suture and its intended use. Also, the packages are designed taking into consderation the economics of the package, the method of placing the sutures in the package, the type of suture placed in the package, etc. In general, the ideal package protects the suture during handling and storage yet allows the suture to be removed with a minimum of difficulty, prevents kinking, knotting, or entangling of the suture and the package itself should be economical to produce.

The more popular suture package consists of a folded paper or cardboard retainer with the sutures therein and with the retainer contained in a sterile hermetically sealed envelope. In many instances, the sterility of the suture and the envelope are maintained by a second sealed outer wrap. When the suture is to be used, the outer wrap is opened in the operating room and the sealed envelope deposited in a sterile area. Sterile personnel thereupon tear open the sterile envelope providing access to the suture.

Many packages have been developed which contain a plurality of sutures and have been designed in such a way as to allow all the sutures to be removed from the package or to allow a single suture to be removed from the package. The packages must be designed so a single suture can be removed from the package of multiple sutures without disrupting or entangling and rendering virtually useless the remaining sutures in the package. One technique for designing such a package is to design the package so it has individual and adjacent compartments with each compartment containing a suture. U.S. Pat. No. 3,759,376 discloses such a package. Another technique for producing such a package is to place some frictional material on the surface of the package which is to engage the sutures. Such frictional material will hold the sutures in place yet will allow a single suture to be removed from the package. An example of such a package is shown in copending U.S. Pat. application Ser. No. 532,632 filed Sept. 15, 1983.

Yet another technique for producing a multistrand suture package allowing for single strand suture dispensing is to wind the sutures in a very specific manner so that they lay in the package in a manner that will allow single strand delivery from the wind. An example of such a technique for winding sutures in such a suture package is dislcosed in U.S. Pat. No. 4,089,409. Still other multistrand suture packages are dislcosed in U.S. Pat. Nos. 4,126,221 and 4,253,563.

Most of the above-described packages are for use with single armed sutures, i.e., a suture having a needle at one end. There have also been a number of packages developed for use with double armed sutures, i.e., sutures having needles at both ends. Examples of such double armed suture packages are shown in U.S. Pat. Nos. 3,759,376, 4,034,850 and 3,985,227. While a number of the above-described packages have gained considerable acceptance for packaging certain types of multistrand sutures to provide for single strand delivery, those sutures which are made of a material that tends to take a set or become kinked when wound still tend to become entangled or kinked or otherwise disrupted when packaged in such packages. One technique for packing multistrand sutures made of materials which tend to take sets is disclosed in U.S. Pat. No. 4,242,898. In this package there is a channel and the sutures are laid in the channel so that as one suture is removed from the channel the other sutures remain in the channel. The economics of this package are not as good as might be desired and, hence, it is still important to develop an economical package that can be used with sutures made from materials that take a permanent set and can be used with monofilament sutures and provide for single strand delivery from a package containing multiple strands of such sutures.

In producing such a multistrand suture package a number of things are important. Perhaps of primary importance is that the sutures should be wound in a manner that reduces the possibility of the suture taking a permanent set. The suture package should hold all the sutures while allowing dispensing of individual sutures without disruption or dislodgment or entangling of the remaining sutures in the package. Also perhaps of equal importance is that the single suture should be easily removed from the package with a minimum of force. Of course, in all such suture packages economics and cost are of importance as well as is the simplicity of the package to keep the expense in packaging sutures in such a package to a minimum.

Also, because of the way double armed sutures are dispensed, either or both needles must be accessible from the package. Therefore, many winding methods used for single armed sutures cannot be used with double armed sutures because of a higher propensity to tangle. Double armed sutures can be dispensed either by pulling one of the needles or by pulling both needles. Many users prefer the one needle dispensing method which results in a higher tendency to tangle or kink. It is an object of the present invention to produce a multi strand suture package which will hold sutures, including monofilament sutures, in a configuration such that any permanent set the suture might take is reduced. It is another object of the present invention to produce a multistrand suture package which allows for single strand delivery of sutures from the package with little or no disruption of the remaining sutures in the package. It is still another object of the present invention to have a package which is economical to produce. It is yet another object of the present invention to produce a package which will readily dispense double armed sutures without entanglement of the suture.

These and other objects of the present invention will become more apparent upon the reading of the ensuing description and claims.

SUMMARY OF THE INVENTION

The present invention provides a suture retainer for multiple sutures, especially those sutures that tend to take a permanent set when wound or otherwise configured and even more preferably for such sutures made from monofilaments. Furthermore, the suture retainer provides for single strand delivery of a suture from the retainer and in some of the preferred embodiments of the present invention the retainer provides for the packaging of double-armed sutures; that is, sutures having needles attached to both ends of the suture. The retainer of the present invention comprises a jacket member which totally encloses the sutures and an insert member disposed within the jacket member. The insert member, in the preferred embodiment of the present invention, cooperates with the jacket member to provide a plurality of compartments in which individual sutures are contained. The jacket member has a first panel. The first panel has an oval shaped deflectable portion disposed in said panel. This deflectable portion is foldable away from the first panel to provide an oval opening in the first panel. The oval opening allows the panel to be placed over a plurality of pins about which the sutures to be packaged are wound. By providing such an opening, sufficient pins may be placed about the periphery of the opening to allow the suture to be wound in a relatively smooth curve, rather than being wound back and forth between two pins which requires a tight curve about each individual pin. The jacket member includes a second panel foldably connected to the first panel along one edge of the first panel. The second panel is substantially co-extensive; that is, it is substantially of the same size as the first panel so that when the second panel is folded on the first panel it substantially covers the first panel. The jacket member includes a third panel foldably connected to the edge of the first panel opposite the edge to which the second panel is foldably connected. The third panel may be smaller than the first and second panels but should be of such a size to at least partially cover the deflectable portion of the first panel. The jacket member includes a fourth panel which is also foldably connected along one of the other edges of the first panel. The fourth panel is smaller than the first panel but is of such a size to at least partially cover the deflectable portion of the first panel when that fourth panel is folded onto the first or third panel. The jacket member includes a fifth panel foldably connected to the edge of the second panel opposite the edge to which the second panel is foldably connected to the first panel. The fifth panel is used to interlock all of the folded panels together and in the preferred embodiment this fifth panel includes a tab at its free edge which may be inserted into a slit in the deflectable portion of the first panel to lock all the panels together. The insert member is disposed between the first and second panels of the jacket member when the first and second panels are folded together. The insert member is large enough to cover the deflectable portion of the first panel. The insert member has a plurality of openings disposed about its periphery and within the portion of the insert member covering said deflectable portion. This allows the insert to be placed on top of the pins. The insert may comprise a series of foldably connected panels, all of which have a plurality of openings about their periphery which openings are superimposed one upon another as the insert panels are folded upon one another. In operation, this allows the deflectable portion of the first panel of the jacket member to be placed on the pins and a suture wound about those pins. A panel of an insert member may be then placed over the pins and a second suture wound on the pins and this operation repeated as many times as there are panels on the insert member. This provides separate compartments for the individually wound sutures.

In a preferred embodiment of a retainer of the present invention, the first panel of the jacket member also includes means for holding needles, said means being disposed along an edge of the first panel spaced from the deflectable portion. A preferred means for holding such needles with the needles being attached to the sutures is a foam member with slits in the foam member in which the needles may be located.

In another preferred embodiment of the present invention, the second panel of the jacket member may have a perforated or partially cut portion extending from one edge of the panel into the panel which edge may be readily torn to expose a portion of the sutures and in the preferred embodiment to expose the needles attached to the sutures.

In certain embodiments of the present invention, the jacket member and the insert member with a plurality of sutures appropriately disposed therein is hermetically sealed in an outer envelope. Preferably, the outer envelope comprises a pair of heat sealable films, sealed about the periphery of the folded suture retainer (jacket and insert members) to hermetically seal the folded retainer therein. In some of the embodiments where there is a tear strip; that is, a perforated line along the second panel, the second panel will also include a tab adjacent such precut line which tab can be sealed into the periphery of the hermetically sealed outer envelope. It is preferred that a notch or some indication be placed in the periphery of some outer envelope to indicate where the pre-cut line originates. This allows the outer envelope to be torn open at such indication or insert which will automatically tear the pre-cut line in the second panel and expose a portion of the sutures to the user, preferably the needle portion, which is attached to the sutures.

The invention will be more fully described when taken in conjunction with the accompanying drawings.

DETAILED DESCRIPTION OF THE INVENTION

Figure 1:
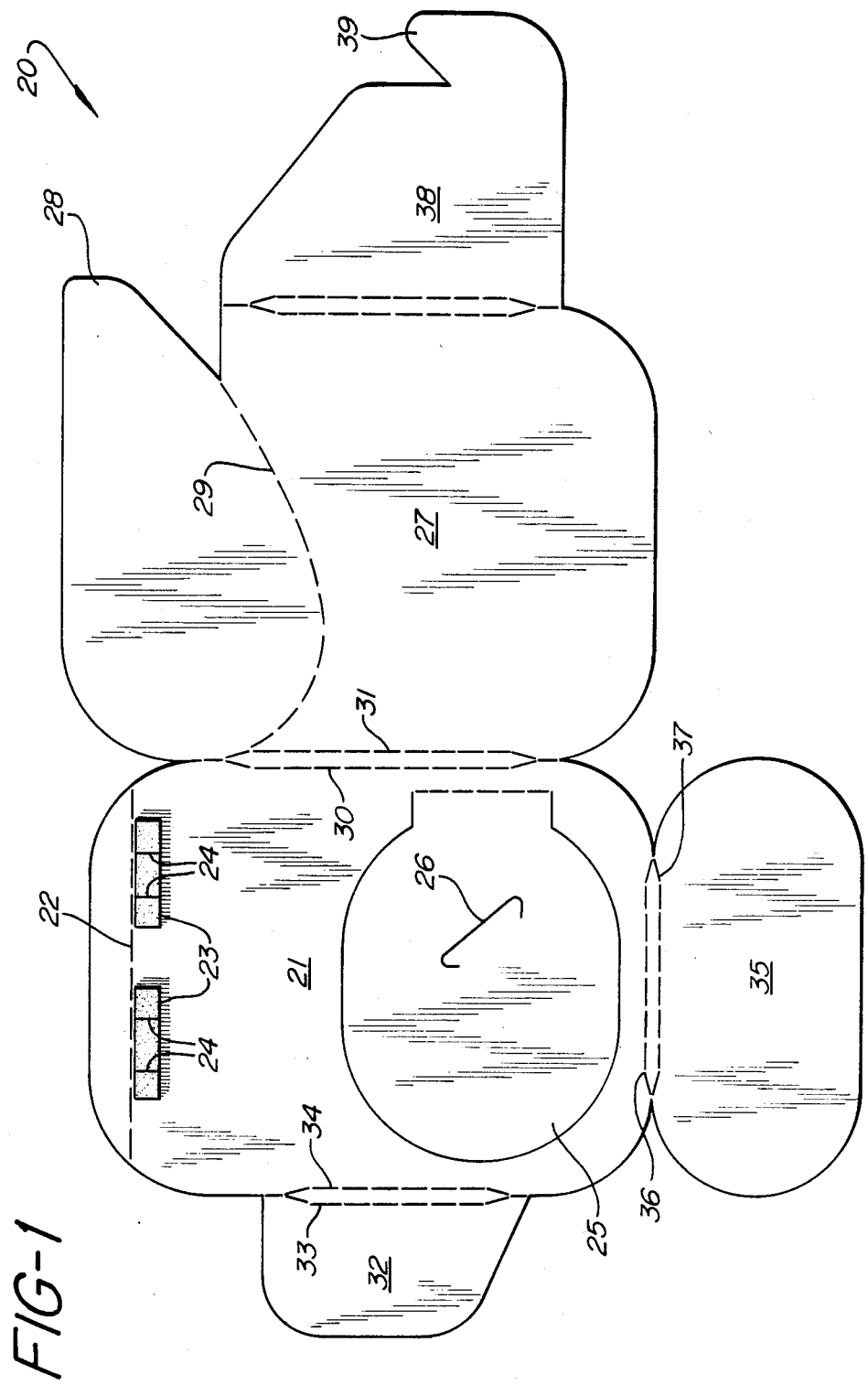
FIG. 1 is a plan view of a jacket member of a suture retainer in accordance with the present invention with that jacket member in its completely unfolded condition.

In FIGS. 1–9 the same numeral is used in all Figures to indicate each of the various elements of the suture retainer for the present invention. In FIG. 1 there is shown the jacket member 20 of the present invention. The jacket member comprises a first panel 21 which is somewhat longer than it is wide. At the top of the panel there is a fold line 22 running transverse of the panel and immediately disposed below this fold line are needle holding means 23. In this embodiment, the needle holding means comprises pieces of foam with slits 24 in the foam for insertion of the needle and suture to be placed in the retainer. The bottom portion of the first panel contains a deflectable portion 25 which is generally oval shaped. The purpose of this deflectable portion will be further described in conjunction with the drawings. Disposed in the center of the deflectable portion is a diagonal slit 26, the purpose of which will also be described in conjunction with ensuing figures. Foldably connected along one of the longer sides of this first panel is a second panel 27. The second panel is substantially the same size as the first panel. In the upper right-hand corner of this panel there is a tab 28, the purpose of which will be disclosed when describing the other figures. Extending from the tab and disposed diagonaly across the second panel is a pre-cut line 29 or perforated line to allow this portion of the panel to be torn away from the fully folded retainer to expose the foam needle holding members holding the sutures and needles. The foldable line connecting the first and second panel is a double fold line 30 and 35 to form a gusset and provide some depth between the panels to allow for the disposition of the sutures between panels. Connected to the opposite longer edge of the first panel is a third panel 32. This third panel is smaller than the first panel but is sufficiently large to cover at least a portion of the deflectable portion of the first panel. The foldably connected line also is a double line 33 and 34 forming a gusset.

Foldably connected to one of the shorter sides of the first panel is a fourth panel 35. The fourth panel is foldably connected to the shorter side of the first panel opposite the suture holding means. The foldably connected line is a double line 36 and 37 forming a gusset. The fourth panel is also smaller than the first panel but is sufficiently large to cover a portion of the deflectable portion of the first panel. Foldably connected to the longitudinal edge of the second panel opposite the edge connected to the first panel is a fifth locking panel 38. This panel has a tab 39 at its free end for interlocking with the slit in the deflectable portion of the first panel. The fifth panel is connected to the second panel by a double foldable line similar to the fold lines connecting the other panels.

Figure 2:
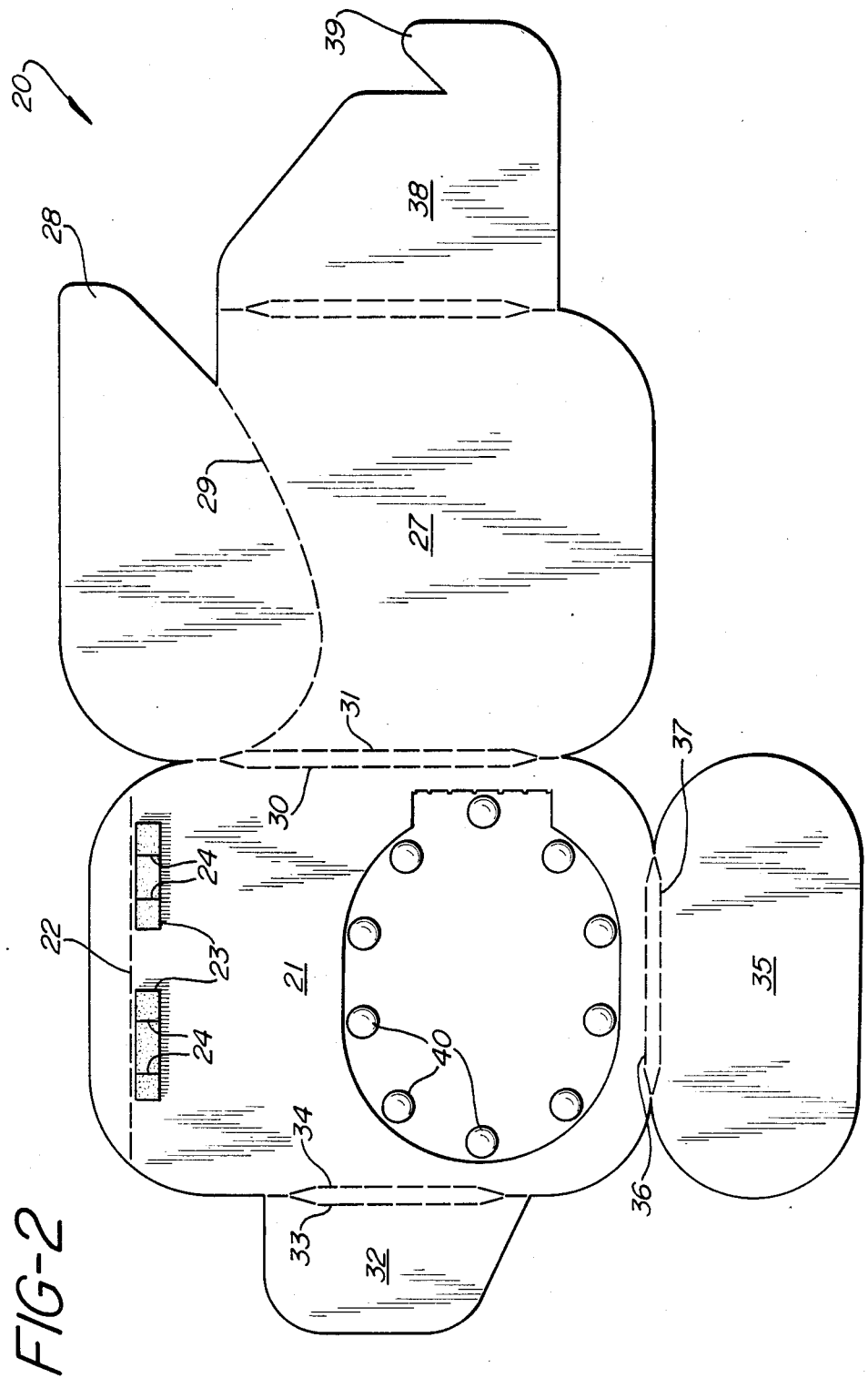
FIG. 2 is a plan view of the jacket member of FIG. 1 with the deflectable portion folded back and the member placed about a set of winding pins.

Referring to FIG. 2, the deflectable portion of the first panel is bent back away from the first panel so that the deflectable portion is disposed beneath the second panel. The jacket is then placed over a pluraltiy of pins 40 with the pins disposed in a generally oval configuration so that the pins extend through the oval opening in the first panel and are positioned substantially around the periphery of the oval opening.

Figure 3:
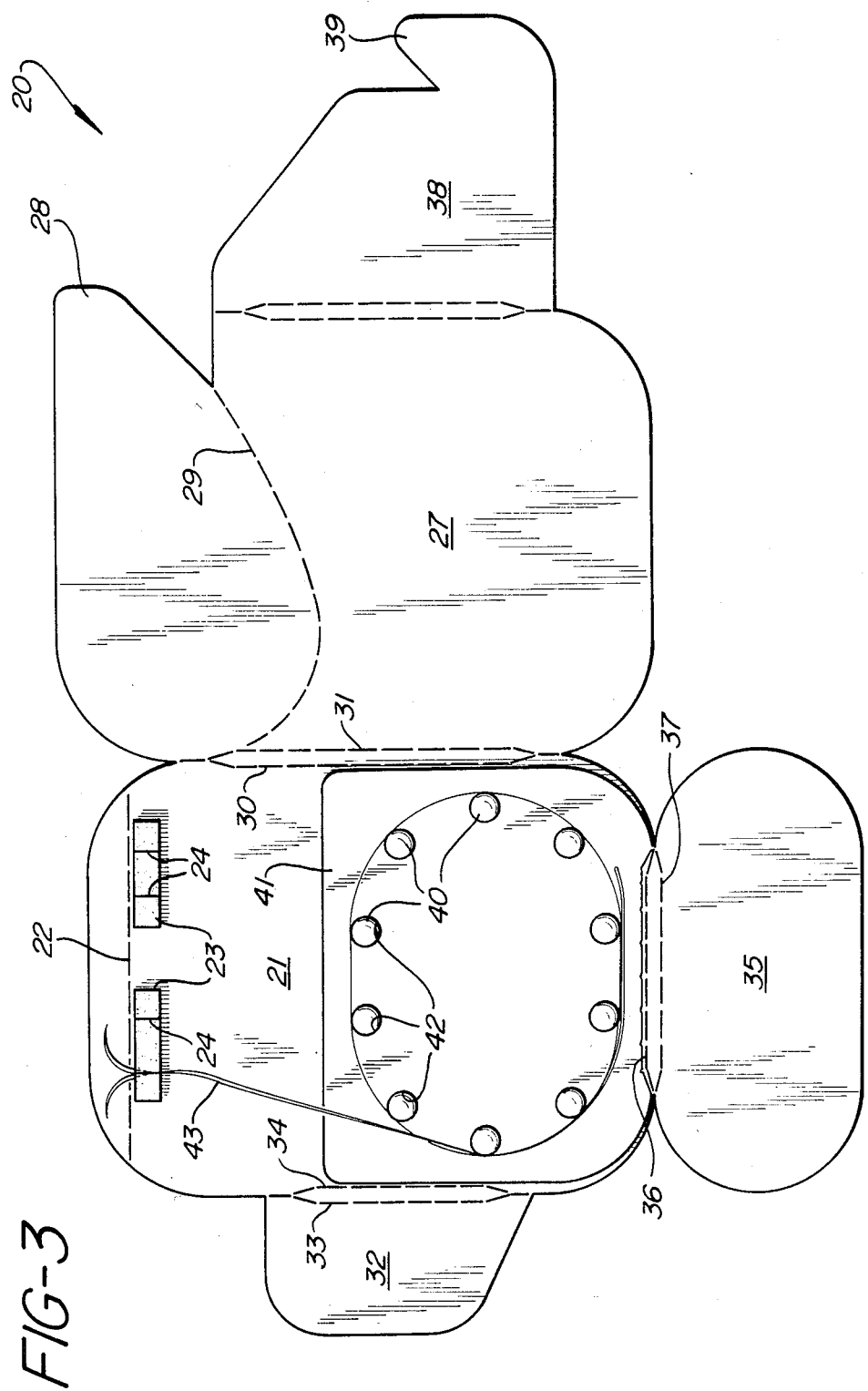
FIG. 3 is a plan view of the jacket member of FIG. 2 with an insert member placed on the jacket member in a first double-armed suture wound about the pins.

In FIG. 3, the jacket member with the deflectable portion turned back to expose the oval opening has been placed on the pins and on top of the pins is an insert member 41 which covers the entire opening and has a plurality of openings 42 disposed in the insert member through which the pins extend. In this embodiment, a double-armed suture 43; that is, a suture with a needle attached to both ends of the suture, is wound about the pins by first placing the needles in a slit in the needle holding means and then winding the free end about the periphery of the plurality of pins.

Figure 4:
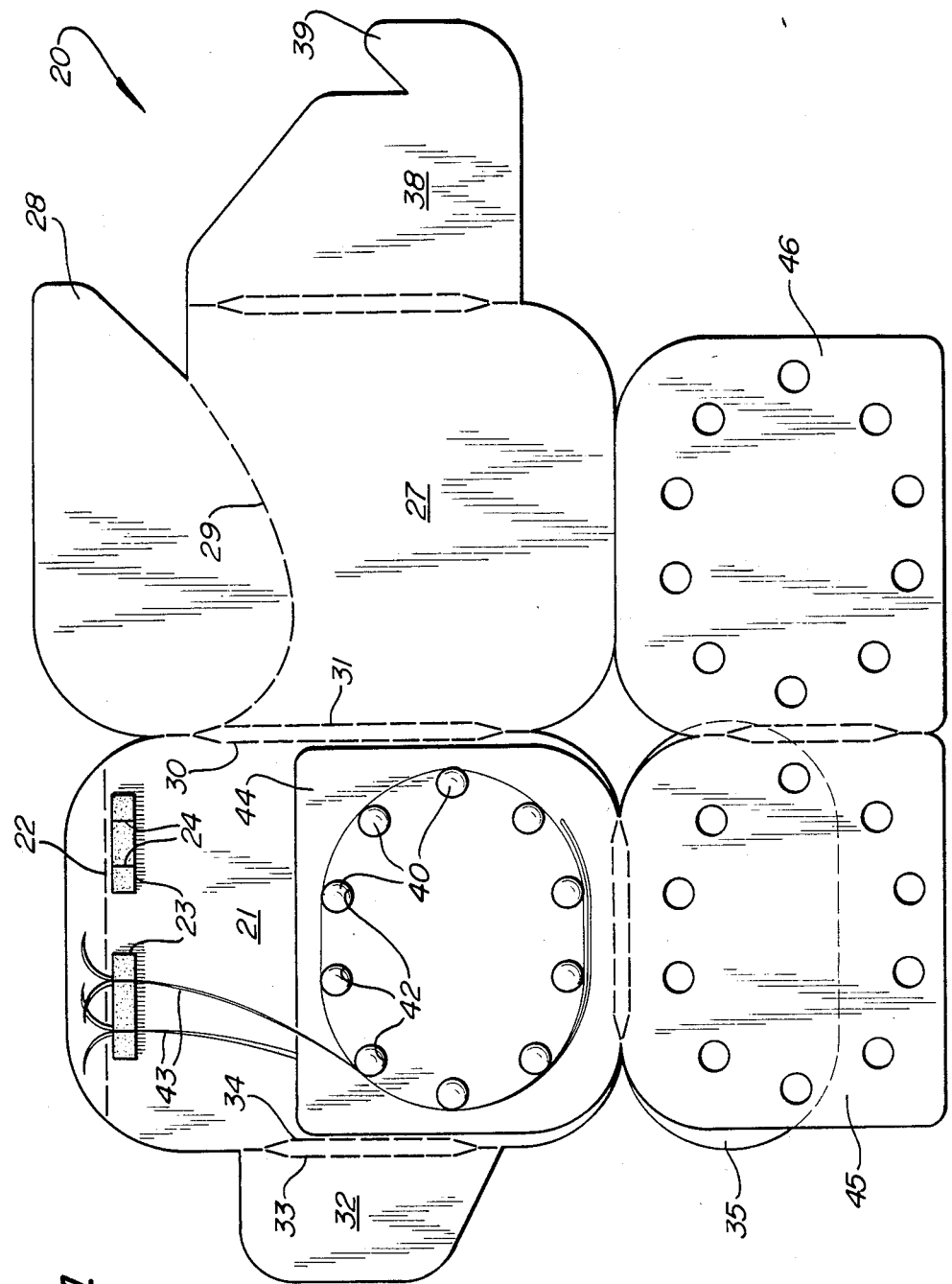
FIG. 4 is a plan view of the jacket member of FIG. 3 with a second insert member placed on the jacket member and with a second suture wound about the pins.

In FIG. 4, after that first double-armed suture has been wound, a second insert member comprising three sections, 44, 45 and 46 each of substantially the same size and shape as the first insert member is placed on the pins as shown. These panels are foldably connected to each other as shown. One of the second insert member section 44 is placed over the wound suture and a second double-armed suture 45 has the needles first placed in the needle holding means and is then wound about the pins on top of section 44. This procedure is followed again by folding on top of the previously wound suture a second section 45 of the insert member and winding a third suture on top of that section. The last section 46 is then folded on top of that third wound suture and another suture wound on top of that section.

Figure 5:
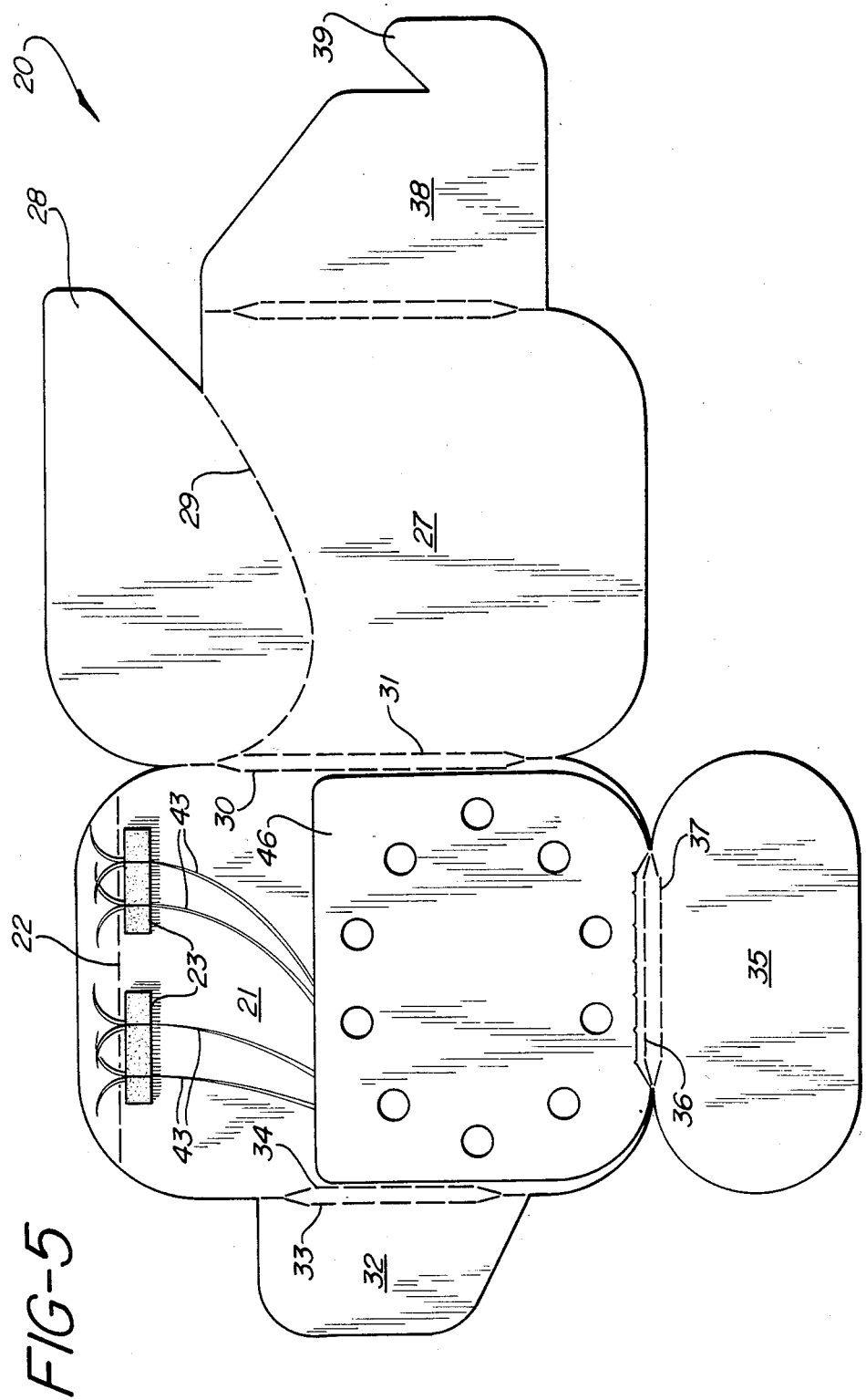
FIG. 5 is a plan view of a suture retainer with the jacket member in its unfolded condition and the insert member in its completely folded condition and with sutures in place in the insert member.
Figure 6:
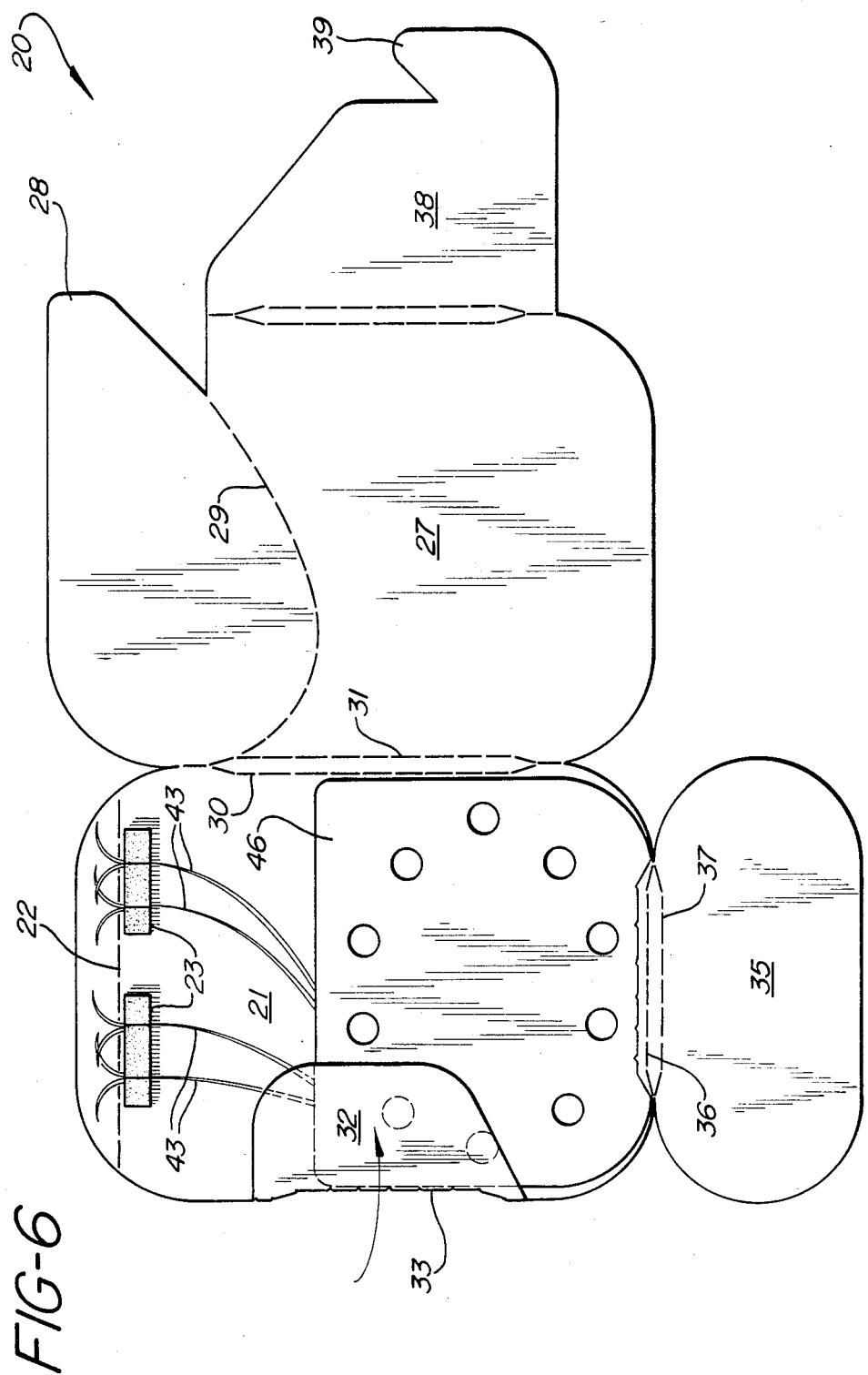
FIG. 6 is a plan view of the jacket member and insert member of FIG. 5 with the third panel folded on the insert member.
Figure 7:
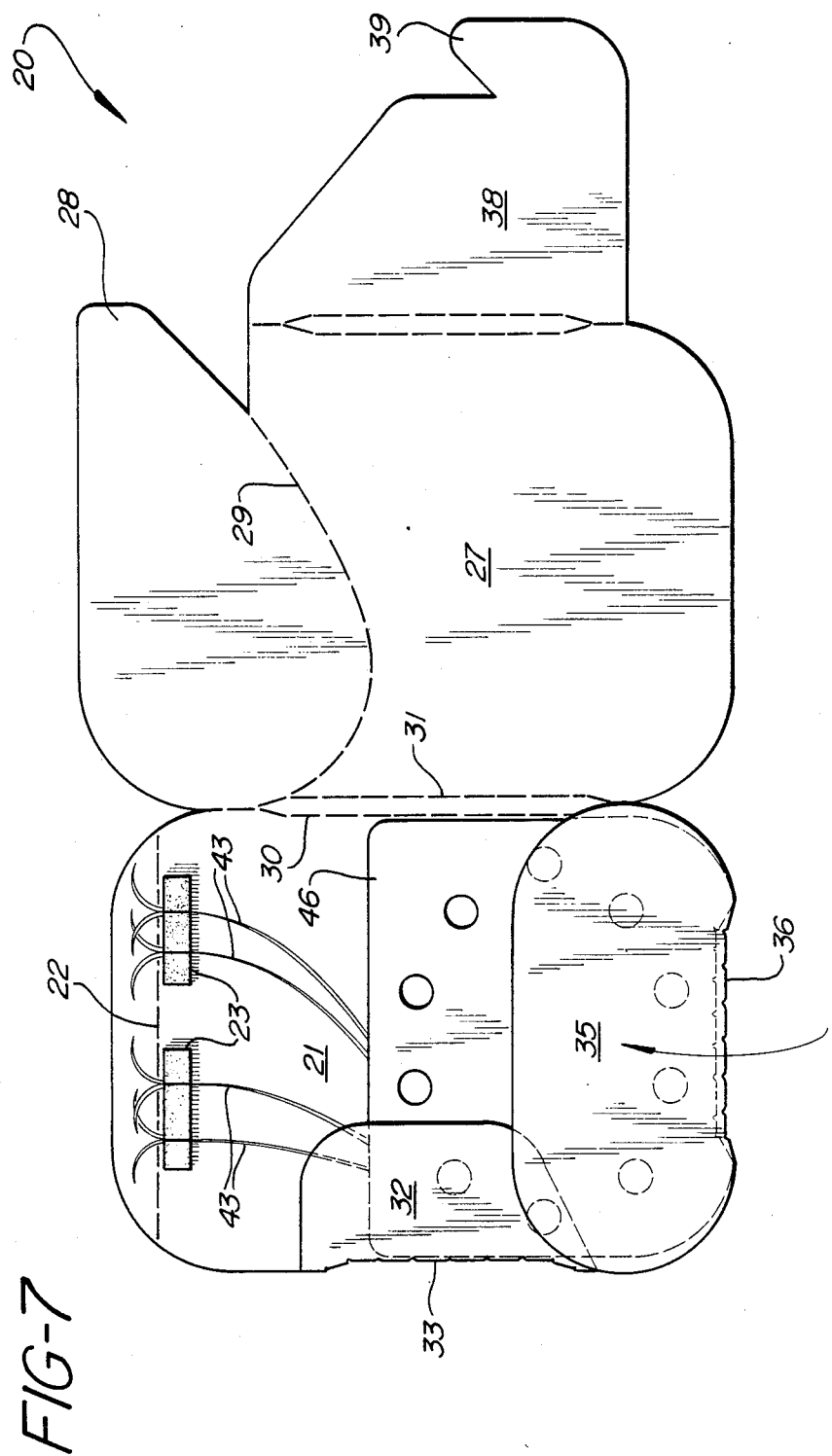
FIG. 7 is a plan view of the retainer of FIG. 6 with the fourth panel in its folded condition.

In FIG. 5 the last panel of the insert member has been folded on top of the wound sutures and then as depicted in FIGS. 6 and 7, the third panel 32 is folded on top of the insert member and the fourth panel 35 is also folded on top of the insert member.

Figure 8:
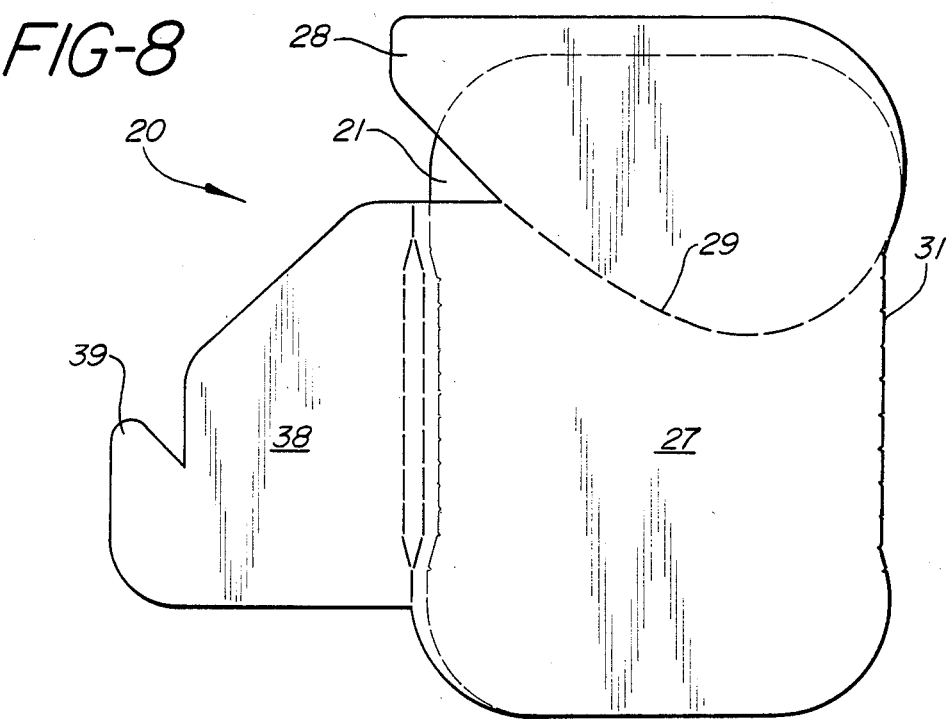
FIG. 8 is a plan view of the suture retainer of FIG. 7 with the second panel folded on top of the first, third, and fourth panels.
Figure 9:
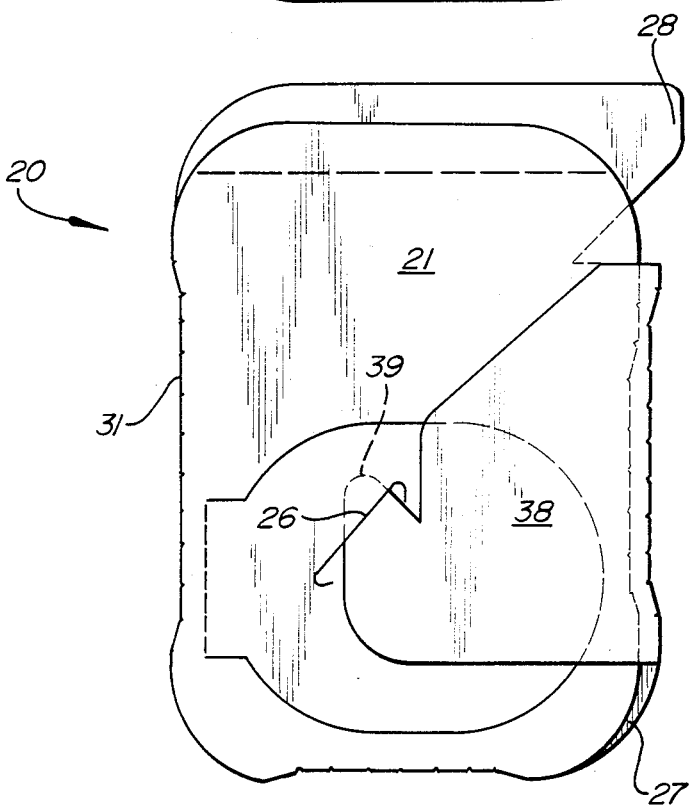
FIG. 9 is a plan view of the fully folded and interlocked suture retainer of the present invention.

As depicted in FIG. 8, the second panel 27 is then folded on top of the first, third, and fourth panels to totally enclose the sutures and needles. The fifth panel 38 of the jacket member is then folded behind the first panel and the tab of the fifth panel is inserted in the slit in the deflectable portion of the first panel to lock the entire panels together as shown in FIG. 9.

Though in the specific embodiment described double-armed sutures have been used, of course, single-armed sutures may also be wound in a similar manner or even unarmed sutures may even be wound in a similar manner.

Also in the specific embodiment shown two separate insert members have been used—one being a single panel and the other being a triple panel, it is within the scope of the present invention to use all single panel insert members or insert members of a plurality of panels or any combinations of the two. The important thing being that each panel of an insert member acts as a separation between individually wound sutures so that single sutures may be removed from the suture retainer without disruption of any other sutures within the retainer. Also, the number of pins is not critical as long as there are at least three or more pins. By providing such a large opening for the pins, it provides for a plurality of pins which means that the suture may be wound in a much more gentle curve or arch about those pins as contrasted to merely utilizing two pins to wind the suture which requires a fairly sharp turn about each pin. This is important when winding sutures that tend to take a permanent set such as monofilament sutures.

The jacket member and insert members of the present invention are preferably constructed of a heavy-weight, relatively stiff sulfate paper board. This paper board is easily foldable and yet sufficiently strong and stiff to support the suture and provide a rigid package. Other material, including plastic, foil, and laminates, combined with each other or with paper, may also be used. the retainer of the present invention may contain sutures of various sizes and lengths as desired and if such various sizes and length are packaged in a single package, they can be identified at the suture holdling means if desired. Also, the retainer may be locked together in its folded condition by various combinations of slits and tabs as is well known in the art. I have merely shown one preferred slit and tab in the preferred embodiment.

Also, though I have shown foam as the preferred holding means, other holding means may also be used to hold the needles and/or ends of the sutures such as pressure-sensitive adhesive and similar gripping means.

Figure 10:
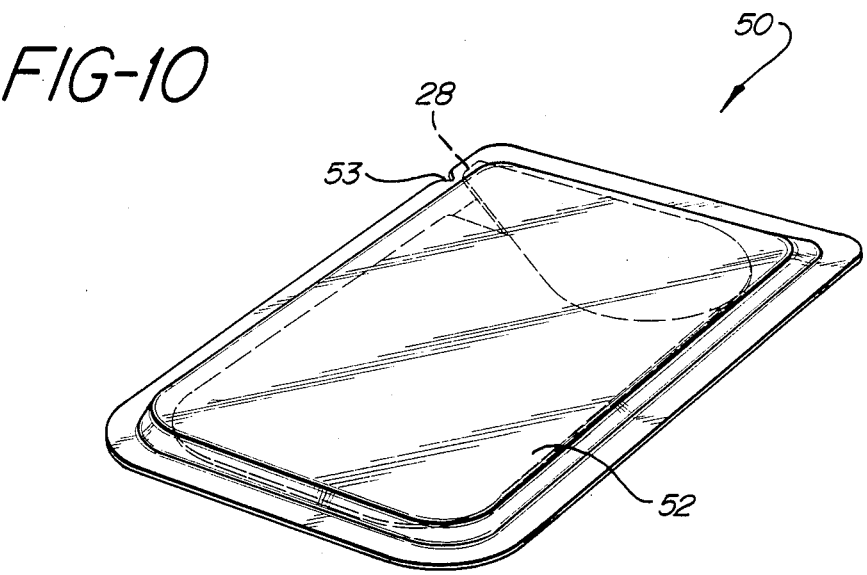
FIG. 10 is a perspective view showing a suture retainer of the present invention in a hermetically sealed package.

The fully folded suture retainer is subsequently sterilized and sealed within sterile outer envelope 50 as illustrated in FIG. 10. The tab 28 on the second suture retainer panel projects beyond the folded retainer 52 and is secured in a sealed area of the envelope as illustrated. A tear notch 53 is provided in the outer edge of the envelope and located approximately adjacent the tab 28 to facilitate the opening of the suture package by tearing the outer envelope. The sutures packaged as illustrated in FIG. 10 are hermetically sealed. The envelope is a conventional suture package envelope formed by heat sealing two panels of aluminum foil coated on their interior surface thereof with a heat sealable polymeric composition. The envelope is bonded around the periphery of the inner suture retainer as illustrated in FIG. 10. Other means for sealing the envelope may be employed as desired.

Figure 11:
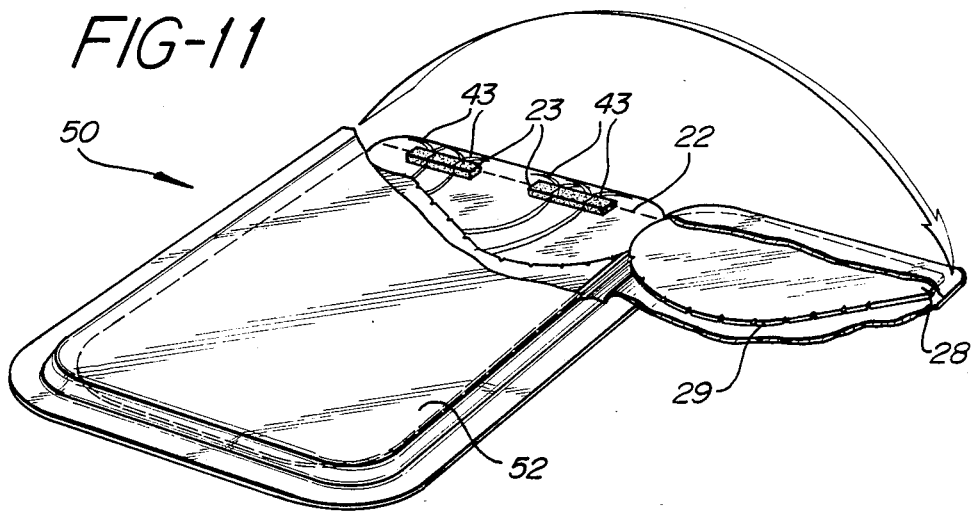
FIG. 11 is a perspective view of a package of FIG. 1 with a portion of the package torn away to expose the needles and sutures.

Sutures packaged as illustrated in FIG. 10 are sterile and hermetically sealed and may be stored for extended periods of time. When the suture is to be removed from the package, the outer envelope is opened by tearing at notch 53 as illustrated in FIG. 11. In the illustrated embodiment where the tab is secured in the sealed enveloped, the precut portion of the second panel of the suture retainer is also torn, exposing the needle holding means and providing ready access to the needles and sutures. It is then a simple matter to grasp the needle with a needle holder to withdraw the suture from between the various panels of the insert member without disrupting any of the other packaged sutures.

Figure 12:
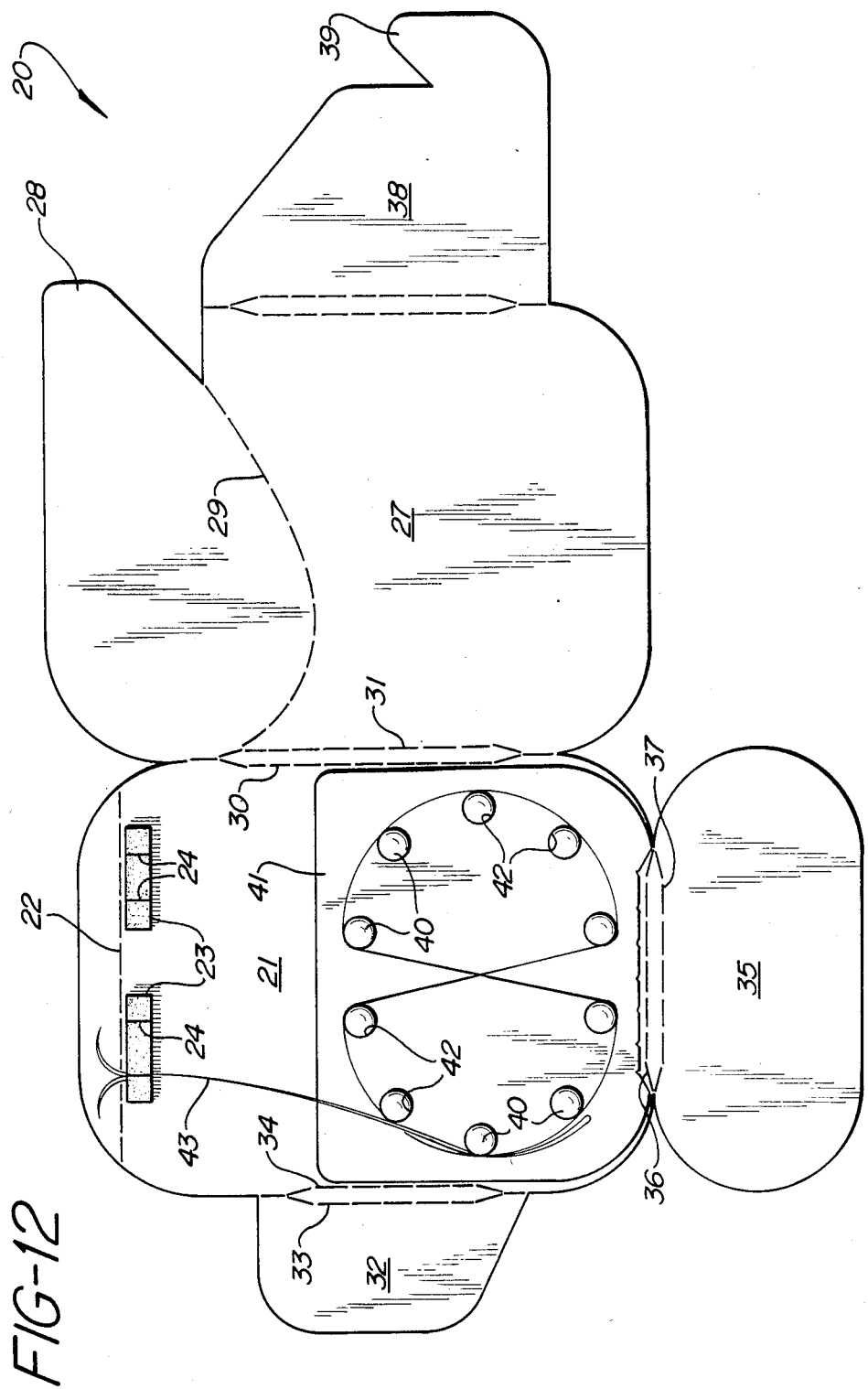
FIG. 12 is a plan view of a jacket member in accordance with the present invention depicting the preferred configuration of a double armed suture in the member.

FIG. 12 shows the same jacket member as depicted in FIGS. 1, 2 and 3, however, the double armed suture is wound in a FIG. 8 wind, with the FIG. 8 perpendicular to the dispensing direction. This FIG. 8 wind perpendicular to the dispensing direction reduces even further the propensity of the suture to tangle when the suture is removed as compared to a circular wind or even a FIG. 8 wind that is parallel to the dispensing direction. The preceding description has been directed primarily to a preferred embodiment of the present invention. Many variations employing the essential features thereof will be apparent to those skilled in the art. Such variations are accordingly included within the scope of the present invention.

I claim:

1. A suture retainer for multiple sutures and providing for single strand delivery of a suture from said retainer, said retainer comprising a jacket member for totally enclosing said sutures and at least one insert member disposed within the jacket member and providing a plurality of compartments for individual sutures, said jacket member comprising a first panel, said first panel having a deflectable portion disposed in said panel, said deflectable portion being foldably away from said first panel to provide an opening in said first panel, a second panel foldably connected to said fist panel along one edge thereof, said second panel being substantially coextensive with said first panel when said second panel is folded on said first panel, a third panel foldably connected to the edge of said first panel opposite the edge to which the second panel is foldably connected, said third panel being of the size to at leat partially cover the deflectable portion when said third panel is folded on said first panel, a fourth panel foldably connected along another edge of said first panel, said fourth panel being of a size to at least partially cover the deflectable portion of said first panel when said fourth panel is folded on said first panel, a fifth panel foldably connected to the edge of said second panel opposite the edge of said second panel foldably connected to said first panel, said fifth panel adapted to interlock with the first panel when the fifth panel is folded about said first panel, said insert comprising a member disposed between the first and second panels when said panels are folded one upon the other, said insert member being large enough to cover the deflectable portion of said first panel and said insert member having a plurality of openings disposed in said member in a manner so that said openings are disposed within the opening formed by the deflectable portion of the first panel.

2. A suture retainer according to claim 1 wherein the deflectable portion has an oval shape to form an oval opening in said first panel.

3. A suture retainer according to claim 2 wherein the plurality of openings disposed in said insert member are disposed about the inner periphery about the deflectable opening of the first panel.

4. A suture retainer according to claim 1 including means for holding needles, said means disposed along one edge of said first panel.

5. A suture retainer according to claim 1 wherein the fifth panel has a tab along its free end and the deflectable portin of said first panel has a diagonal slit disposed in said portion whereby when the retainer is folded the tab is engaged bythe slit to interloc the folded panels together.

6. A suture retainer according to claim 1 wherein the insert member comprises a plurality of foldably connected panels.

7. A suture retainer according to claim 1 or 6 wherein the second panel includes a pre-cut diagonal line extending transversely of the panel to provide for tearing a portion of the panel away to provid access to the needles and sutures in the folded retainer.

8. A suture retainer according to claim 1 or 6 wherein the suture retainer is further packaged in a hermetically sealed envelope.

9. A folded suture retainer according to claim 1 wherein an individual suture is contained in each compartment.

10. A folded suture retainer according to claim 9 wherein the sutures are double armed sutures.

11. A folded suture retainer according to claim 10 wherein the sutures are disposed in a FIG. 8 configuration.

12. A folded suture retainer according to claim 11 wherein the FIG. 8 configuration is disposed perpendicular to the direction from which the sutures are dispensed.

* * * * *